United States Patent [19]

Kooke et al.

[11] Patent Number: 4,670,053

[45] Date of Patent: Jun. 2, 1987

[54] MOLDING MATERIAL AND PROCESS FOR ITS PREPARATION

[75] Inventors: Dieter Kooke, Leichlingen; Peter Schwabe, Leverkusen, both of Fed. Rep. of Germany

[73] Assignee: Bayer Aktiengesellschaft, Leverkusen, Fed. Rep. of Germany

[21] Appl. No.: 743,713

[22] Filed: Jun. 11, 1985

[30] Foreign Application Priority Data

Jun. 30, 1984 [DE] Fed. Rep. of Germany ....... 3424146

[51] Int. Cl.[4] ............................................. C04B 35/68
[52] U.S. Cl. .................. 106/35; 106/38.51; 106/207; 106/209; 433/214
[58] Field of Search ................ 106/35, 207, 212, 272, 106/38.51, 208, 209; 433/214; 523/109

[56] References Cited

U.S. PATENT DOCUMENTS

| | | | |
|---|---|---|---|
| 480,669 | 8/1892 | Norfolk | 106/212 |
| 1,074,600 | 10/1913 | Breyer | 106/212 |
| 4,394,172 | 7/1983 | Scheuble | 106/35 |
| 4,543,372 | 9/1985 | Watanabe et al. | 523/109 |

*Primary Examiner*—Lorenzo B. Hayes
*Attorney, Agent, or Firm*—Sprung Horn Kramer & Woods

[57] ABSTRACT

Impression material in the form of a powder, which, on mixing with water, provides a paste which cures to a solid consistency, the material in the form of a powder being made dust-free by additions of a coating agent, which material is characterized in that it contains paraffin as an additive.

9 Claims, No Drawings

MOLDING MATERIAL AND PROCESS FOR ITS PREPARATION

The present invention relates to an improved, dust-free molding material in the form of a powder, which is based on alginate, and is preferably used for dental purposes, and to a process for its preparation by treatment of the material, in the form of a powder, with certain hydrophobic liquids.

Alginate molding materials have been used for several decades in dentistry, for example for the preparation of molds This entails a particular quantity of water being added to the material, in the form of a powder, immediately before it is used, and stirring it to form a paste which is applied to the article from which it is intended to prepare an impression. After a few minutes, the initially plastic mass solidifies to give a flexible, dimensionally stable gel which reproduces, as a negative, the surface contours of the object from which a mold is desired, and which can be used for the preparation of a positive impression, for example a plaster model of the object. Suitable alginate compositions in the form of a powder are described in, for example, U.S. Pat. Nos. 2,345,255, 2,390,137, 2,397,145, 2,422,497, 2,733,156, 2,878,129, 3,246,998 and Re 23,700, in British Patent Specification No. 518,596 and in DE-OS (German Published Specification) No. 2,511,168.

Molding compositions according to this state of the art have the disadvantage that their components tend to form dusts, and some of them are difficult to wet with water. On opening the storage vessel or on measuring the material, some of the alginate or of the other constituents is lost as a very finely divided dust, and this not only leads to annoyance for the processor but also may be hazardous to health on inhalation of the dust. Moreover, the material in the form of a powder can be mixed with water only with difficulty, and when it is stirred in it floats on the surface of the liquid for a lengthy period.

To avoid these problems, it is proposed in European Patent No. A 58,203 that the impression composition in the form of a powder, or at least one component thereof, be coated with a substance which is soluble, or at least dispersible or wettable, in water. Alginate molding positions which are at present commercially available contain hydrophilic polyethers, for example polypropylene glycol, as coating agents of this type. As has emerged, after curing, molding compositions according to European Patent No. A 58,203 detach relatively poorly from the object from which a mold is desired; moreover, they have a matt surface, and the dispersibility in water is still not completely satisfactory either.

It has now been found that improved, dust-free molding compositions with greater image sharpness and rapid dispersibility in water, which are tractable and, after curing, easily detached from the tooth, are obtained when the mixture of components in the form of a powder is treated with paraffin. This has to be regarded as being particularly surprising, since it was not expected that it would be possible rapidly to disperse in water particles coated on the surface with paraffin, which is very hydrophobic. In fact, alginate compositions treated with other hydrophobic substances, such as, for example, silicone oils (polydimethylsiloxanes), cannot be processed to form pastes because of their poor dispersibility in water.

Thus, the invention relates to an impression material in the form of a powder, which, on mixing with water, provides a paste which cures to a solid consistency, the material in the form of a powder being made dust-free by the addition of a coating agent, which material is characterized in that it contains paraffin as an additive.

The materials according to the invention preferably contain 0.5 to 7% by weight, in particular 2.5 to 5% by weight, of paraffin. The paraffins preferably have a viscosity of 10–100,000 cP/20° C., in particular 20–10,000 cP/20° C. Commercially available liquid paraffins are particularly preferably used according to the invention.

Molding materials based on alginate, as are described, for example, in the abovementioned quoted literature, are preferably made dust-free and more dispersible according to the invention. In general, molding materials of this type contain a soluble alginate (for example the Na and/or K salt of alginic acid) in an amount of, preferably, 8–25% by weight, in particular 10–17% by weight, a metal compound which forms with alginic acid a salt which is insoluble in water (for example Pb, Ca or Mg compounds, such as MgO, $MgCO_3$ or $CaSO_4$) in an amount of preferably, 5 to 40% by weight, in particular 10–25% by weight, a curing retardant (for example an alkali metal phosphate diphosphate, pyrophosphate or polyphosphate) in an amount of, preferably, 0.5–10% by weight, in particular 1–5% by weight, and a filler (for example gypsum, kieselguhr, diatomaceous earth, alumina, talc, etc.) in an amount of, preferably, 25 to 85% by weight, in particular 40–75% by weight. Where appropriate, other additives such as, for example, colorants and flavorings, and compounds which improve the compatibility with gypsum (for example K fluorotitanate or K fluorozirconate) can be present in the molding composition.

The molding materials according to the invention are prepared by adding the paraffin to the mixture of the abovementioned components, in the form of a powder, preferably with the material in the mixer being at elevated temperatures (for example 50°–100° C., in particular 60°–70° C.). This can also be carried out in such a manner that the mixture is heated after addition of the paraffin. It is less preferable to treat only one (or a few) of the components with paraffin and then to add this to the remaining components. The paraffin is advantageously added in a paddle mixer, for example a Lödige mixer, whose wall is provided with nozzles through which the paraffin is sprayed onto the mixture in the form of a powder.

The examples which follow illustrate the present invention. Unless otherwise noted, stated amounts are to be understood to be parts by weight or percentages by weight.

EXAMPLES

An alginate molding composition was prepared by mixing the following components:
Potassium alginate: 15.0%
$CaSO_4$: 10.6%
$MgCO_3$: 1.5%
$Na_4P_2O_7$: 1.5%
$K_2TiF_6$: 3.4%
Kaolin: 10.0%
Talc: 2.1%
Diatomaceous earth: 55.9%

The material in the form of a powder was divided into several portions which were treated with a variety of coating agents in the following manner: the mixture was initially introduced into a powder mixer (plough blade mixer), heated to 60°-70° C. and sprayed from above with the particular coating agent using a spray gun. After 10 minutes, the mixer setting was changed to cooling and it was allowed to cool.

The samples thus coated were tested for their relative liberation of dust. The apparatus used for this is a chamber which has the dimensions 50×50×50 cm and which has an inlet nozzle and an aspiration device having a membrane filter. The pump on the aspiration device is switched on and set to a flow rate of 27 l/min. Using a sample funnel attached to the inlet nozzle, 400 mg of sample are blown by a jet of compressed air into the chamber, and the pump is switched off 4 minutes later. The weight of the dust deposited on the membrane filter, multiplied by the empirical factor of 9.4, indicates the mean dust concentration in the chamber.

The results (dust concentration in mg/m$^3$) are compiled in the table below (means of 5 measurements):

| by weight of coating agent | A | B | C | D | E |
| --- | --- | --- | --- | --- | --- |
| 1 | 408 | | | 263 | 376 |
| 2 | 395 | | | 235 | 328 |
| 3 | 386 | | 228 | 216 | 244 |
| 4 | 365 | | 222 | 197 | |
| 5 | 348 | 300 | 179 | 178 | |

A —glycerol
B —polydimethylsiloxane (500 cP/20° C.)
C —polydimethylsiloxane (100 cP/20° C.)
D —liquid paraffin with 180 cP/23° C. (according to the invention)
E —polyethylene glycol Samples coated with substances B and C could not be stirred into water.

Analogous results were obtained with liquid paraffin of viscosity 70 cP/23° C. and the following alginate formulations (data in % by weight):

| K or Na alginate | 12.8 | 14.4 | 16.5 | 17.0 | 14.0 |
| --- | --- | --- | --- | --- | --- |
| CaSO$_4$.2H$_2$O | 2.8 | 7.8 | 28.0 | 9.4 | 11.0 |
| MgO | 3.6 | 9.4 | 10.4 | 4.6 | |
| NaF | | | | 0.7 | |
| K$_2$TiF$_6$ | 2.8 | | | 2.0 | 2.0 |
| Na$_4$P$_2$O$_7$ | 0.2 | 0.8 | 3.9 | | |
| Na$_3$PO$_4$ | | | | 0.7 | 2.0 |
| Na$_2$SiF$_6$ | | 3.1 | | | |
| K$_2$ZrF$_6$ | | | | 3.8 | |
| Al silicate | | | | | 9.0 |
| Kieselguhr | | | | | 62.0 |
| Diatomaceous earth | 77.6 | 64.5 | 37.4 | 65.5 | |

It is understood that the specification and examples are illustrative but not limitative of the present invention and that other embodiments within the spirit and scope of the invention will suggest themselves to those skilled in the art.

What is claimed is:

1. In an impression material in the form of a powder, which on mixing with water provides a paste which sets to a solid consistency, comprising a powder containing a water-soluble alginate or ingredients which form such an alginate, which powder is made dust-free by addition of a coating agent, the improvement wherein the coating agent comprises paraffin.

2. An impression material according to claim 1, wherein the paraffin is present in about 0.5–7% by weight.

3. An impression material according to claim 1, wherein the paraffin is present in about 2.5–5% by weight.

4. An impression material according to claim 1, wherein the paraffin has a viscosity between 10 and 100,000 cP/20° C.

5. An impression material according to claim 1, wherein the paraffin has a viscosity between 20 and 100,000 cP/20° C.

6. An impression material according to claim 1, wherein the powder contains a metal salt and alginic acid which forms therewith a salt which is insoluble in water, a curing retardant and an inorganic filler.

7. A process for the preparation of a molding material according to claim 1, comprising adding paraffin with stirring to a mixture of the components in the form of a powder, or to a portion thereof.

8. A process according to claim 7, wherein the paraffin treatment is carried out at 50°–100° C.

9. In the making of a dental impression by mixing a powder impression material with water to form a moldable paste, and taking a dental impression which said paste and allowing it to set to a solid consistency, the improvement wherein said powder impression material contains a paraffin as a coating agent, whereby the mixing with water does not generate dust.

* * * * *